United States Patent [19]
Kobashi

[11] Patent Number: 5,777,372
[45] Date of Patent: Jul. 7, 1998

[54] DIAMOND FILM BIOSENSOR

[75] Inventor: Koji Kobashi, Kobe, Japan

[73] Assignee: Kabushiki Kaisha Kobe Seiko Sho, Kobe, Japan

[21] Appl. No.: 609,613

[22] Filed: Mar. 1, 1996

[30] Foreign Application Priority Data

Mar. 1, 1995 [JP] Japan ................................. 7-042211

[51] Int. Cl.$^6$ ............................. H01L 27/14; H01L 29/82; B05D 5/12
[52] U.S. Cl. .................. 257/414; 427/53.1; 427/55; 427/56.1
[58] Field of Search ................ 427/53.1, 55, 56.1, 427/446, 450, 458, 596; 257/414

[56] References Cited

U.S. PATENT DOCUMENTS 5,154,945  10/1992  Baldwin et al. ................... 427/596

*Primary Examiner*—Carl W. Whitehead
*Attorney, Agent, or Firm*—Oblon, Spivak, McClelland, Maier & Neustadt, P.C.

[57] ABSTRACT

A diamond film biosensor has a transducer that is partially or totally composed of semiconducting diamond film and/or undoped diamond film. A bioidentifier is fixed partly or entirely on the surface of said semiconducting diamond film and/or undoped diamond film. The peripheral circuits are partly or entirely composed of undoped diamond film and/or semiconducting diamond film. The diamond film biosensor can detect chemical substances and biosubstances with a high sensitivity and fast response, has a long lifetime, and is reusable.

19 Claims, 15 Drawing Sheets

DIAMOND FILM BIOSENSOR

BACKGROUND OF THE INVENTION

1. Technical Field of the Invention

This invention relates to a diamond film sensor that can be suitably used as a biosensor or a chemical sensor used in such fields as medical care, food processing, industrial processes or environmental monitoring.

2. Prior Art

Diamond is featured by various excellent characteristics such as heat resistance and large bandgap (5.5 eV). Although undoped diamond film is electrically insulating, it can be semiconducting by doping impurities such as boron (B). Electronically, diamond has excellent characteristics such as high breakdown voltage and high saturation drift velocity as well as low dielectric constant.

By fully making use of these characteristics of diamond, electronic devices such as temperature sensor, rectifying diode, and field effect transistor using semiconducting diamond have been developed. Also, by utilizing the large bandgap of diamond, applications to photosensors or light emitters in the short wavelength range such as ultraviolet have been studied.

Besides the electrical characteristics, diamond has excellent properties, far superior to other substances, that the thermal conductivity is high, the specific heat is low, it is stable against chemical reagents, and it is highly resistant to heat and radiation of radioactive rays.

In spite of such excellent properties of diamond, not many studies have been done in semiconductor applications, except for electronic devices such as temperature sensors, diodes, transistors, and the like to be used at high temperature based on diamond's high resistance to heat.

In recent years, extensive studies have been done on biosensors that detect physical and chemical changes by sensing electrical signals at the electrode, where bio-related materials to discriminate and identify biological and chemical materials in the testing sample (which will be hereafter referred to as "bioidentifiers"), such as enzymes, antigens, antibodies, organelles, animal and plant cells, binding proteins, microorganisms, which react only with specific chemical substances and biosubstances, are fixed. FIG. 27 shows the concept of such biosensors.

Among many biosensors, most widely used is a glucose sensor. It is usually composed of two electrodes: the first electrode is to detect oxygen or hydrogen peroxide, and glucose oxidase is fixed on the second electrode. The glucose concentration in the sample to be tested is determined by detecting, via electrodes, the decrease of oxygen concentration due to the oxygen consumption when glucose is converted to gluconolacton under a catalytic reaction with glucose oxidase, or by detecting the increase in hydrogen peroxide concentration due to the hydrogen peroxide generation by the same reaction. In this case, glucose oxidase is said bioidentifier.

The present inventors found that since diamond has an excellent biocompatibility, semiconducting diamond film can be synthesized by vapor-phase growth methods, and the micro-fabrication of diamond film is possible, diamond film can be applied to transducers (signal converting circuits) and peripheral circuits for a wide range of biosensors. Since diamond consists of covalently bonded carbon atoms, diamond is nontoxic to said bioidentifiers and has a strong affinity to them. Furthermore, since the surface of diamond can be chemically modified to be either hydrophilic or hydrophobic, it is possible to make it anti-thrombogenic.

However, so far the biocompatibility of diamond has been considered to be used only for coatings on artificial organs, and no application has been considered by concurrently making use of both the semiconducting characteristics and the biocompatibility of diamond.

For instance, in the references: (1) X. Zhang et al., Proceedings of the 2nd International Conference on the Applications of Diamond Films and Related Materials, edited by M. Yoshikawa et al. (MYU, Tokyo 1993), p. 65; (2) X. Zhang et al., Materials Letters, Vol. 18, pp. 318–319 (1944); and (3) J. Zhu et al., Biosensors & Bioelectronics, Vol. 9, pp. 295–300 (1994), a non-diamond material was coated on a diamond film which was used only as a base substrate for a glucose sensor. These are hereafter referred to as the prior art 1.

In the prior art 1, the diamond film was used merely to improve the adhesion of metal electrodes to the base substrate, and therefore the diamond base substrate could be replaced by other materials. Furthermore, in the prior art 1, the diamond film was not directly in contact with the sample substance to be inspected, and as a result, the biocompatibility of diamond was not utilized at all.

Attempts of using diamond film as a chemical electrode have been reported in the references: (1) K. Patel et al., Collection of Published Articles by Joint Research in the Japan Solar Energy Society and the Japan Wind-Power Energy Association (Sept. 20–21, 1991), pp. 105–108; (2) K. Patel et al., J. Photochem. Photobil. A: Chem., Vol. 65, pp. 419–429 (1992); (3) R. Tenne et al., J. Electroanal. Chem., Vol. 347, pp. 409–415 (1993); (4) S. Yang et al., Advances in New Diamond Science and Technology, edited by Y. Saito et al., (MYU, Tokyo 1994), pp. 741–744. These are hereafter referred to as the prior art 2. The prior art 2 showed that in electrolysis, reductive reactions proceed efficiently by using semiconducting diamond as the electrode.

However, the prior art 2 is aimed at the application of diamond electrode in chemical industries, and therefore neither the application of diamond film for biosensors nor the microfabrication of biosensors is described at all.

As shown in FIG. 1, a method of using diamond film or diamond-like film as a gate insulating film for Ion Sensitive Field Effect Transistor (hereafter abbreviated as ISFET) made of silicon semiconductor is presented in the Japanese Patent Provisional Publication No. 86-33645. This is hereafter referred to as the prior art 3. In FIG. 1, the source 4 and the drain 5, composed of an n-type diffusion layer of silicon, are formed on the surface of a p-type silicon substrate 6, on which the first insulating film 1 and said diamond film or diamond-like film 2 are deposited as the gate insulating film 3.

In order to deposit a high quality diamond film, it is known that the temperature of the substrate on which diamond is deposited must be kept at about 800° C. However, at such a high temperature, the ISFET composed of silicon semiconductor are thermally damaged. Therefore, it is impossible to use the prior art 3 for practical applications when diamond film is used as the gate insulating film 2.

In order to extend the lifetime of biosensors, it is necessary to prevent detachment and flow-out of said bioidentifiers, and the following arts have been proposed for a fixation of said bioidentifiers on electrodes. In the Japanese Patent Provisional Publications Nos. 85-29657, 85-39547 and 85-79258, a method is presented, wherein said bioidentifier and photosensitive resin (photoresist), used in the photolithography process for semiconductor microfabrication, are mixed and coated on the ion sensitive surface of ISFET, and polymerized by an illumination of ultraviolet light. In the Japanese Patent Provisional Publication No. 85-247151, another method is proposed, wherein an organic film having an affinity to said bioidentifier is coated on the surface of the gate area to fix said bioidentifier. In the Japanese Patent Provisional Publication No. 88-229358, another method is proposed to make the surface insoluble after the above processes. This is hereafter referred to as the prior art 4.

In the methods hereabove described, since said bioidentifiers are mixed with photosensitive resins, the kind of usable photosensitive resins is limited, and the mixing may cause a problem that the activity of said bioidentifiers is reduced. The activity of said bioidentifiers is further reduced in the processes of ultraviolet radiation and photolithography using developers and removers. Furthermore, in order for the biosensors to function, both chemical substances or biosubstances in the sample to be inspected and the by-products generated by the reactions between chemical substances or biosubstances and said bioidentifiers must diffuse across the photosensitive resin. However, the diffusion velocity of chemical substances or biosubstances is in general low, so that the response speed of the biosensors of this kind is also low accordingly. Therefore, a significantly long time is needed until the electrical signals from the biosensors are stabilized.

On the other hand, the following technologies have been proposed to prevent the flow-out of said bioidentifiers. The Japanese Patent Provisional Publication No. 85-173459 shows a method, wherein after said bioidentifier is coated on the electrode, it is further laminated with a porous material. In the Japanese Patent Provisional Publication Nos. 86-88135 and 86-234349, a method is proposed to prevent the flow-out, wherein the molecules of said bioidentifiers are mutually bound by bridging reactions. However, these methods also have the same problems as hereabove described.

The following structures are known for biosensors:

(1) In FIG. 2, a working electrode 9 for sensing and a counter electrode 8 are formed on a planar substrate 7, and a reference electrode 10 is provided. Said bioidentifier 11 is coated on said working electrode 9, and the insulating resin 12 is coated in the central part of the sensor (see Japanese Patent Provisional Publication No. 85-174359). This is hereafter referred to as the diode-type sensor.

(2) FIG. 3 shows another type of sensor, wherein a microarray of electrodes is used in the diode-type sensor (see prior art 4, for example, Japanese Patent Provisional Publication No. 85-247151). This is hereafter referred to as the microarray-type sensor. A silicon oxide film 14 is formed on a silicon substrate 13, and a silicon oxide film 15, used for a separation of each element, is selectively deposited on the silicon oxide film 14. In the area surrounded by the silicon oxide film 15, a chloromethyl polystyrene film 16 is deposited between said working electrodes 17 and said counter electrodes 18, and the enzyme 19 is fixed on the chloromethyl polystyrene films.

(3) FIG. 4 shows another type of sensor, wherein said bioidentifier is fixed on the gate portion of ISFET so that it can respond to changes in ion concentration or pH (see Japanese Patent Provisional Publication No. 93-281181). This is hereafter referred to as the transistor-type sensor. Here, a gold film 21 is deposited on the back side of a sapphire substrate 20, and FET 26 of npn-structure is fabricated on the surface of the sapphire substrate 20. A silicon oxide film 22 and a silicon nitride film 23 are deposited to cover the FET 26, on which albumin 24 and glucose oxidase 25 are fixed.

(4) FIG. 5 shows another type of sensor, wherein said bioidentifier 28 is fixed on a thermistor circuit 27. This figure illustrates a sensor to detect the increase in temperature caused by heat generated by the reaction between said bioidentifier fixed on the circuit and chemical substances or biosubstances in the sample to be inspected (see Japanese Patent Provisional Publication No. 86-212750). This is hereafter referred to as the thermistor-type sensor.

(5) As shown in FIG. 6, in the Japanese Patent Provisional Publication No. 93-256812, another type of sensor is proposed, wherein a counter electrode 8, a working electrode 9, and a reference electrode 10 are formed on the diode-type biosensor substrate 7 in the same way as shown in FIG. 2. Here, said bioidentifier 11 is fixed to the working electrode 9, and the heater 29 is formed in the surrounding area to control the temperature.

However, for the biosensors shown in FIGS. 2–6, since metal is used as the electrodes, it is difficult to fix said bioidentifiers on them, as detachment or flow-out of said bioidentifiers occurs during the operation. Therefore, a problem exists in those cases that the lifetime of the sensor is short. Likewise, in the ISFET shown in FIG. 4, silicon oxide (a ceramic material) is used as an insulating film at the gate area, and thus the same difficulty as hereabove described occurs in fixing said bioidentifiers.

SUMMARY OF THE INVENTION

It is an objective of the present invention to provide a diamond film biosensor that can satisfy all the requirements of high sensitivity, long lifetime, fast response, and reusability, and solve the problems that have existed in the past.

A diamond film biosensor according to the present invention comprises a transducer, partially or totally composed of semiconducting and/or undoped diamond film, where said bioidentifier is fixed in the partial or entire area of the surface.

The usage of diamond film for a biosensor has the following merits: since both diamond and said bioidentifiers are composed of carbon in terms of the chemical structure, diamond is intrinsically compatible with said bioidentifiers. Furthermore, the affinity of diamond with said bioidentifiers can be improved by chemical modification of the diamond film surface, and hence a good adhesion of bioidentifiers with diamond film can be achieved.

Regarding the vapor-phase synthesis of diamond film, microwave plasma chemical vapor deposition (CVD) (e.g., Japanese Patent Publication Nos. 84-27754 and 86-3320), radio-frequency plasma CVD, hot filament CVD, direct-current plasma CVD, plasma jet, combustion method, and thermal CVD are known.

Diamond films produced by the vapor-phase synthesis hereabove described on non-diamond substrates are generally polycrystalline, i.e., an aggregation of randomly oriented diamond particles, containing grain boundaries at high density in the film. However, it is recently reported that highly oriented diamond films, wherein diamond crystal particles are oriented in the same direction, can be synthesized by a special pretreatment of the substrate surface prior to diamond CVD.

It is also possible to synthesize polycrystalline diamond films and highly oriented diamond films, where the film surface is composed only of either (111) or (100) crystal faces of diamond.

In the deposition of diamond film on bulk diamond, diamond films with an arbitrary crystal plane can be prepared, because the bulk diamond can be cut and polished along the desired crystal plane.

Diamond can be semiconducting by adding a very small amount of impurities to the source material. For instance, p-type semiconducting diamond with a good electrical conductivity can be prepared by adding boron (B) as the impurity in both high temperature-high pressure synthesis and vapor-phase synthesis of diamond.

In the present invention, said transducer can be fabricated using semiconducting diamond film on which said bioidentifier is fixed, thus providing a biosensor with a high sensitivity, long lifetime, and fast response, that is reusable.

Since diamond is used partially or totally for the active area of said biosensor, the biocompatibility of diamond can be utilized to the best advantage.

In case that the sensitivity of diamond film biosensor is deteriorated, it can be restored by chemically removing said bioidentifier and other materials from the electrodes, and re-fixing said bioidentifier and other necessary materials on the electrodes.

In the present invention, the useful properties of diamond, i.e., biocompatibility, inertness against chemical reagents, nontoxicity, etc., are fully utilized as said transducers are made of semiconducting diamond film and/or undoped diamond film with said bioidentifiers fixed.

Moreover, since hydrophilicity and hydrophobicity of diamond surface can be controlled by chemical treatment, the diamond biosensors can have an anti-thrombogenic property.

In the present invention, said biosensor can have a structure of diode, transistor, thermistor, and magnetic sensor, or these sensor structures can be fabricated monolithically on the same substrate.

Finally, it should be noted that the sensitivity of the diamond biosensors can be increased by an illumination of light on the transducer area.

DETAILED DESCRIPTION OF THE PREFERRED EMBODIMENTS

Figure 7:
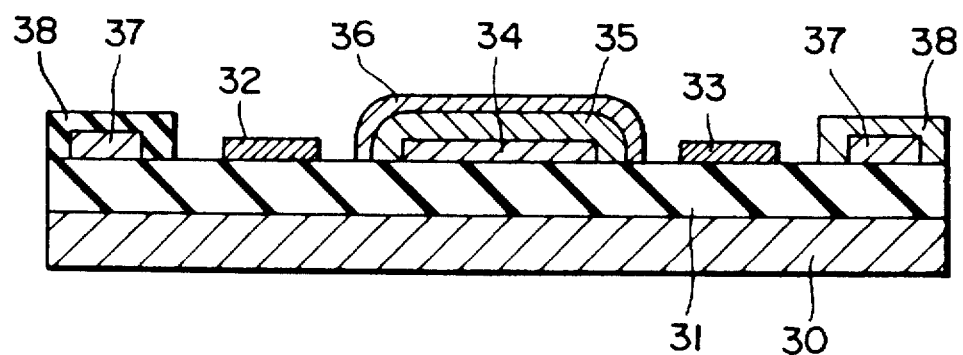
FIG. 7 is a cross-sectional view of a diode-type diamond sensor, according to the embodiment of the present invention.

Detailed description of the present invention is given by referring to the attached drawings below. FIG. 7 illustrates a cross-sectional view of said transducer of said diode-type sensor using diamond film. The microfabrication of diamond film can be performed using known technologies such as selective deposition, plasma etching, and micromachining. For example, the microfabrication technology of diamond or selective deposition technology, which are necessary for the production of said transducers, was reported in the reference: T. Inoue et al., J. Appl. Phys., Vol. 67, No. 12, pp. 7329–7336 (1990).

Peripheral circuits, such as a heater to heat said transducer and a temperature sensor to measure the temperature of the sample, can be made using said semiconducting diamond films. The manufacturing of both the transducer and the peripheral circuits in a monolithic manner would have a merit in terms of function and cost.

In FIG. 7, an undoped diamond film 31 as the base layer is formed on the substrate 30, and working electrode 34, counter electrode 33, and reference electrode 32 are formed on said undoped diamond film 31. The working electrode 34 is coated with said bioidentifier 35, which is further coated with a biomembrane 36.

The working electrode 34, counter electrode 33, and reference electrode 32 are surrounded by a semiconducting diamond heater 37, which is coated with an undoped diamond film 38.

In FIG. 7, said undoped insulating diamond film 31 is used as the base layer. However, note that a biosensor structure without the base layer is possible. This is the case for any of the forms of the biosensors described in this invention.

In case that diamond film is used for electrodes, the base layer, and the heater, there is no restriction in size for the biosensor: the optimum size can be selected, depending on such parameters as the boron doping concentration in the diamond film. However, it is recommended from a viewpoint of performance and cost that the thickness of the undoped diamond base layer 31 is between 1 and 50 µm, the thickness of the electrodes 32–34 is between 0.1 and 5 µm, the length and the width in the active area of the electrodes 32–34 is between 20 µm and 1 mm, the thickness of the heater 37 is between 0.1 and 50 µm, and the thickness of the undoped diamond film 38 for electrical insulation is between 0.5 and 10 µm.

Figure 8:
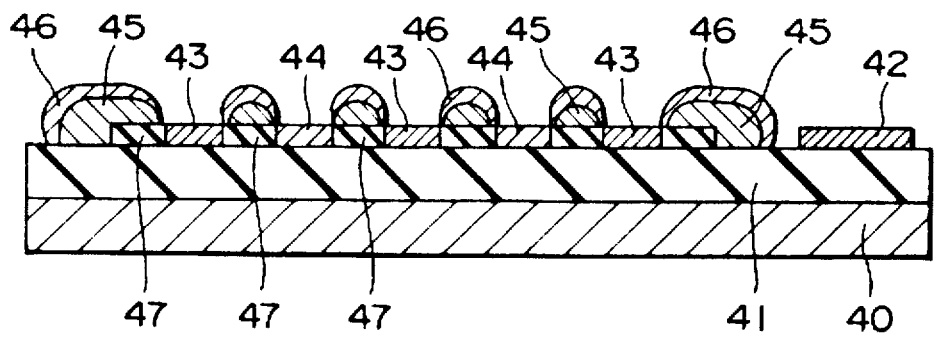
FIG. 8 is a cross-sectional view of a microarray-type diamond sensor provided in the embodiment of the present invention.
Figure 9:
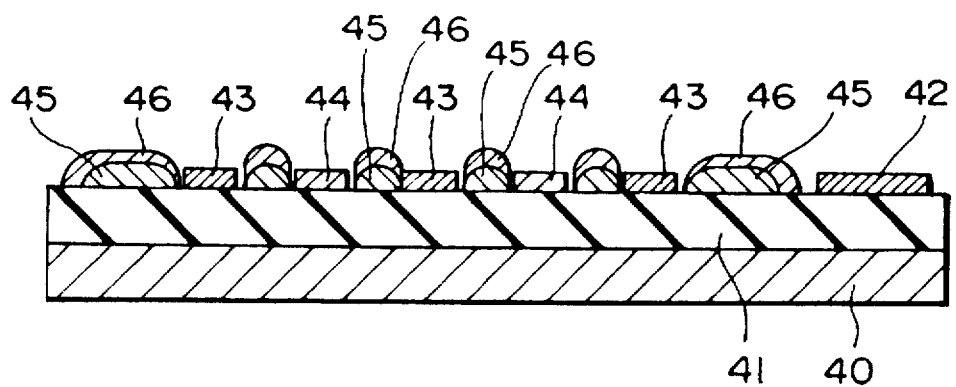
FIG. 9 is a cross-sectional view of another microarray-type diamond sensor provided in the embodiment of the present invention.

FIGS. 8–11 illustrate a cross-sectional view of each of said transducers of microarray-type. In FIG. 8, an undoped diamond film 41 is formed on the substrate 40 as the base layer, and an undoped diamond film 47 is placed between the multiple counter electrodes 43 and the working electrode 44 on the base layer (undoped diamond film) 41. Also, said undoped diamond film 47 is placed outside said counter electrodes 43. A bioidentifier 45 is fixed on said undoped diamond film 47, and said bioidentifier 45 is coated with a biomembrane 46. Moreover, a reference electrode 42 is formed on said undoped diamond film 41.

Figure 1:
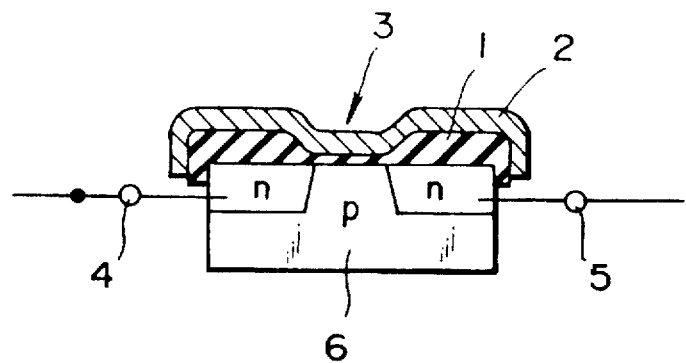
FIG. 1 illustrates a conventional transistor-type sensor.
Figure 2:
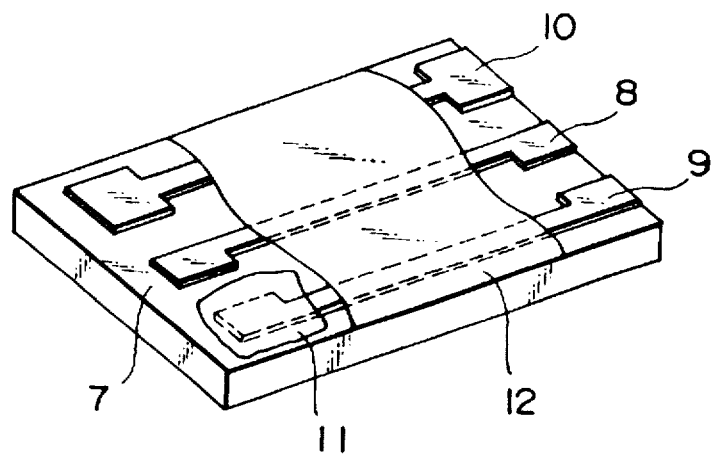
FIG. 2 illustrates a conventional diode-type sensor.
Figure 3:
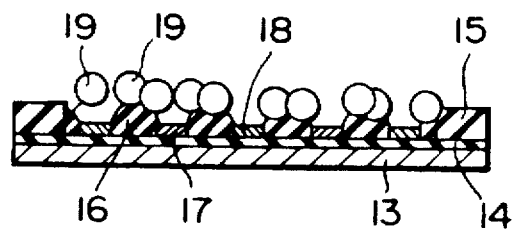
FIG. 3 illustrates a conventional microarray-type sensor.
Figure 4:
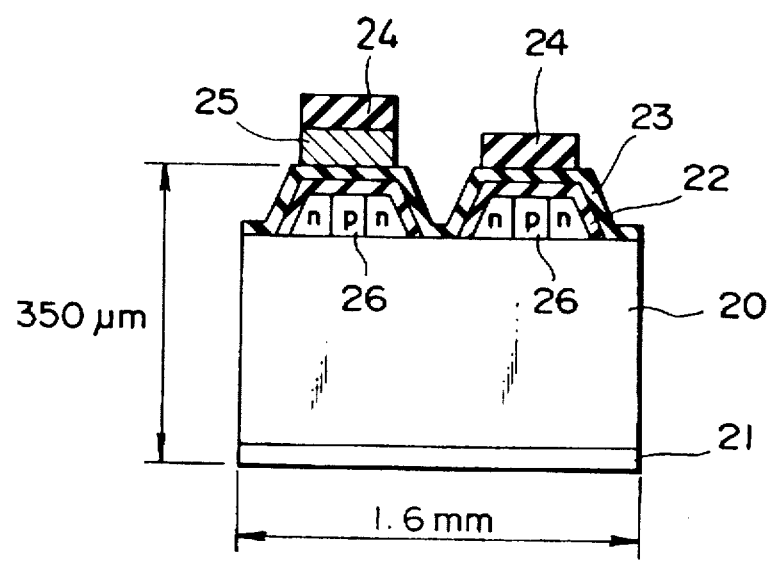
FIG. 4 illustrates a conventional glucose sensor using ISFET.
Figure 5:
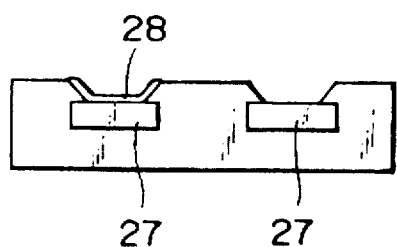
FIG. 5 illustrates a conventional thermistor-type sensor.
Figure 6:
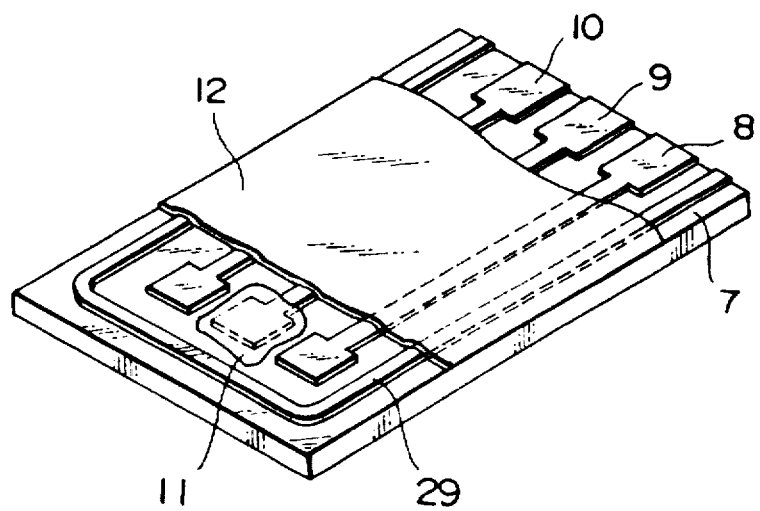
FIG. 6 illustrates a conventional biosensor with a built-in heater.

As illustrated in FIG. 8, if said bioidentifier 45 is fixed on said undoped diamond film 47 placed between said working electrode 44 and said counter electrode 43, or if said undoped diamond film 47 is used as the base layer, as illustrated in FIG. 3, said undoped diamond film 47 placed between the working electrode 44 and the counter electrode 43 is not always necessary and can be omitted. In this case, the bioidentifier 45 can be fixed on said undoped diamond film 41 used as the base layer.

Figure 10:
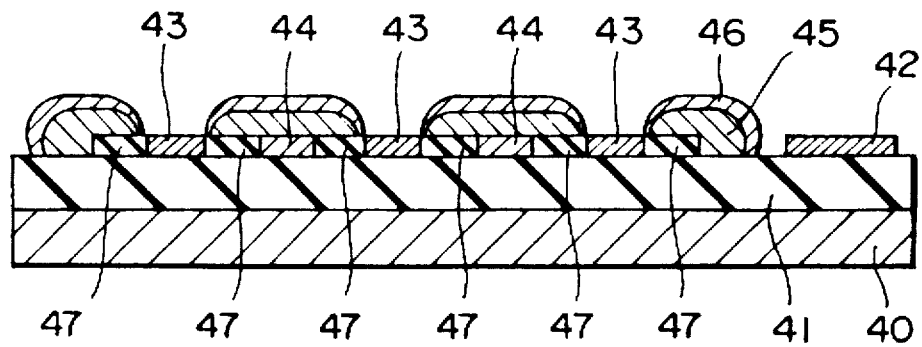
FIG. 10 is a cross-sectional view of another microarray-type diamond sensor provided in the embodiment of the present invention.
Figure 11:
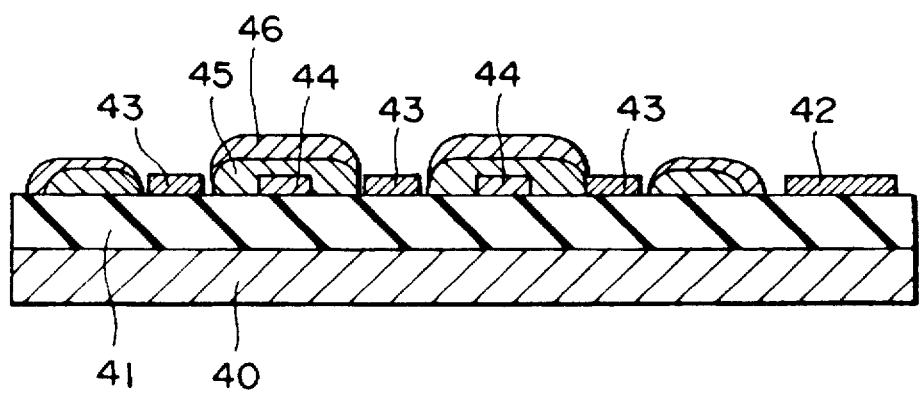
FIG. 11 is a cross-sectional view of another microarray-type diamond sensor provided in the embodiment of the present invention.

Any of the working counter, and reference electrodes can be semiconducting diamond film as in the case of diode-type biosensors. As illustrated in FIGS. 10 and 11, said working electrode 44 can be semiconducting diamond film on which said bioidentifier 45 is fixed, as in the case of diode-type biosensors.

In the microarray-type sensor, as in the case of the diode-type sensor, there is no limitation in size for the electrodes and the base layer, and the optimum size can be selected, depending on such parameters as the boron doping concentration in the diamond film. However, it is most desirable that the width and the length of the active diamond film electrodes can be between 1 and 20 µm, and between 20 µm and 1 mm, respectively.

Figure 12:
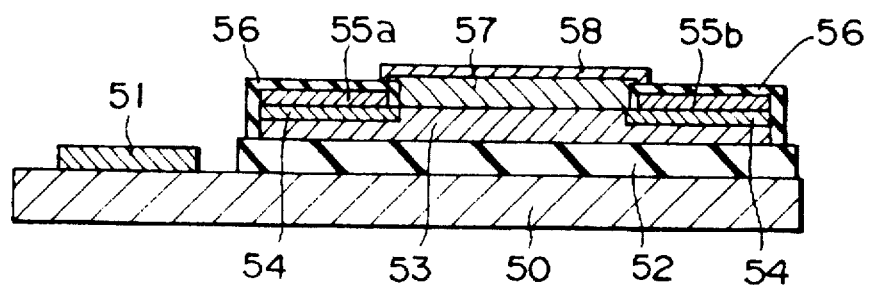
FIG. 12 is a cross-sectional view of a transistor-type diamond sensor provided in the embodiment of the present invention.

When the transducer is of transistor type, the transistor can be made of semiconducting diamond film. FIGS. 12–15 illustrate diamond sensors of transistor type. FIG. 12 is the case that the transistor is MESFET (Metal-Semiconductor FET).

In FIG. 12, an undoped diamond film 52 and a gate electrode 51 are formed on a substrate 50, and a semiconducting diamond film 53 is formed on said undoped diamond film 52. Two heavily boron (B)-doped (p$^+$) diamond layers 54 are formed on the surface of said semiconducting diamond film 53, and a source electrode 55a and a drain electrode 55b are formed on the p$^+$ diamond layer 54. The p$^+$ diamond layer (hereafter referred to as the p$^+$ layer) can be formed by ion implantation or vapor-phase synthesis, where boron is introduced at high concentration ($10^{19}$ to $10^{22}$ atom/cm$^3$).

Said source electrode 55a and drain electrode 55b are coated with an electrically insulating film 56, which is composed of electrically insulating materials, such as silicon dioxide, silicon nitride, and resins, or a multiple layer of these materials. The contact resistance between said electrodes 55a and 55b and said semiconducting diamond layer 53 is reduced by the existence of said p$^+$ layer 54 directly under said source electrode 55a and said drain electrode 55b.

A bioidentifier 57 is fixed between said source and drain electrodes (the total portion composed of said bioidentifier 57 fixed between the two electrodes is referred to as the gate portion), and its surface is covered with a biomembrane 58 for stabilization.

The voltage applied to said gate electrode 51 can be either negative or positive with respect to said source electrode 55a, but the sensitivity of the biosensor can be usually higher at negative voltage.

According to the studies by the present inventors, when the material of the substrate 50 is not diamond, it is desirable that the thickness of said undoped diamond base layer 52 is between 1 and 20 µm, the thickness of said p$^+$ layer 54 is between 100 µm and 1 mm, the thickness of said semiconducting diamond layer 53 is between 100 µm and 2 mm, and the distance between said source and drain electrodes (hereafter, referred to as the gate length) is between 0.5 and 50 µm. The signal current is greater as the horizontal width of the source and drain electrodes (hereafter referred to as the gate width) is larger. It is preferable that the gate width is between 2 µm and 1 mm. If the material of the substrate 50 is diamond, it is desirable that its thickness is between 20 and 500 µm.

Figure 13:
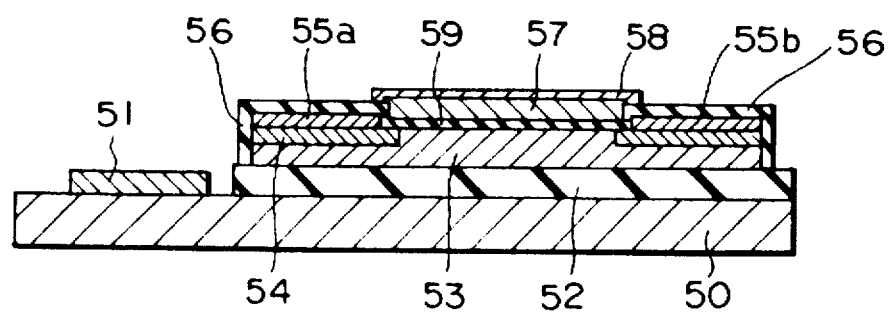
FIG. 13 is a cross-sectional view of another transistor-type diamond sensor provided in the embodiment of the present invention.

FIG. 13 illustrates a transistor-type sensor using MiSFET (Metal-intrinsic semiconductor-Semiconductor FET) as a transducer. Here, the undoped diamond film 59 is deposited on the surface of the semiconducting diamond layer 53 (hereafter, this undoped diamond film 59 is referred to as the gate insulator). The most desirable length of each part of this sensor is the same as those described above. It is most preferable that the thickness of the gate insulator 59 is between 100 µm and 1 mm.

Figure 14:
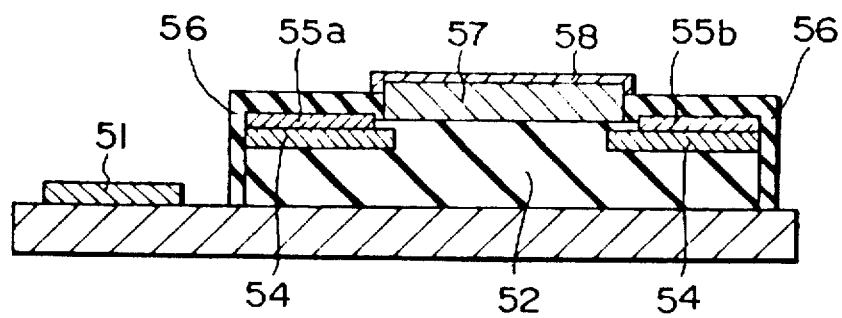
FIG. 14 is a cross-sectional view of another transistor-type diamond sensor provided in the embodiment of the present invention.

FIG. 14 illustrates a transistor-type biosensor using pip-FET as a transducer. A biosensor of this type has no semiconducting diamond layer 53. Note that the p$^+$ layer 54 under the drain electrode 55b is not always necessary and can be omitted. The most desirable length of each part is the same as those described above. The thickness of the undoped diamond film 52 is between 1 and 10 µm, and the thickness of the gate insulator 59 is between 0.5 and 1 µm.

Figure 15:
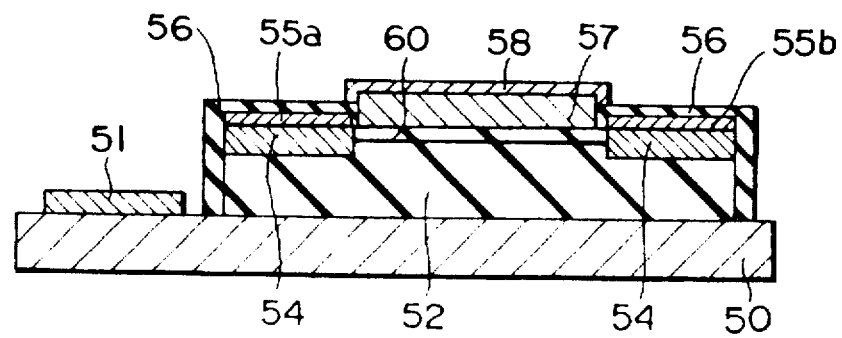
FIG. 15 is a cross-sectional view of another transistor-type diamond sensor provided in the embodiment of the present invention.

FIG. 15 is an example using a δ-doped FET as a transducer. The p$^+$ layer 54 under the source and drain electrodes is connected by a thin semiconducting diamond layer 60 doped with boron at high concentration. The most desirable length of each part is the same as in the case of the pip-FET, and the most desirable width of the thin film semiconducting diamond layer 60 is between 50 and 500 µm.

As illustrated in FIGS. 12–15, said bioidentifier 57 is fixed on the gate portion. However, it is possible to attach said bioidentifier 57 only around the FET. In this case, the by-products, generated by the reaction between the bioidentifier and the chemical and bio-related substances in the sample to be inspected, changes the voltage at the gate portion, which is then detected as a current change in the FET, and hence the concentration of the chemical and bio-related substances in the sample to be inspected can be determined.

Figure 16:
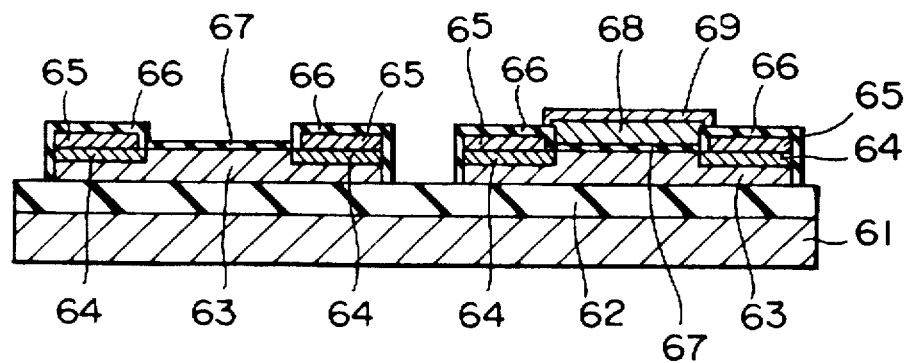
FIG. 16 is a cross-sectional view of a thermistor-type diamond sensor provided in the embodiment of the present invention.
Figure 17:
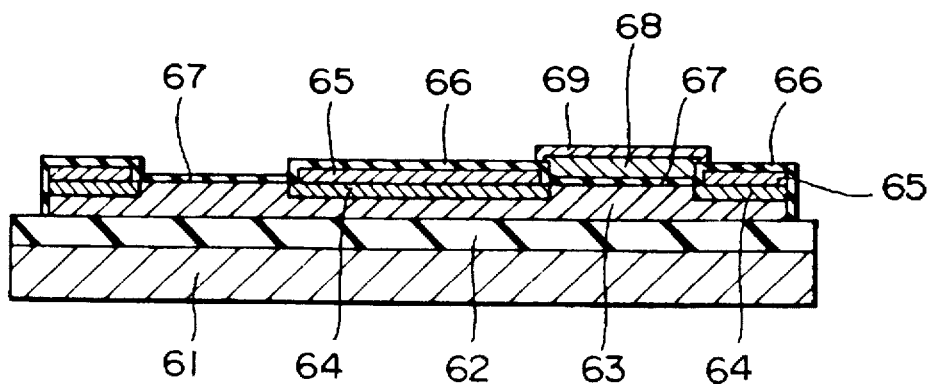
FIG. 17 is a cross-sectional view of another thermistor-type diamond sensor provided in the embodiment of the present invention.

If the transducer is of thermistor type, the concentration of the chemical and bio-related substances is determined by the change in temperature due to the heat generated by the reactions between the bioidentifier and the chemical and bio-related substances contained in the sample. FIGS. 16 and 17 illustrate thermistor-type diamond sensors using diamond films.

In FIG. 16, an undoped diamond base layer 62 is formed on a substrate 61, on which a thermistor for heat measurement and a thermistor for reference are monolithically fabricated using a semiconducting diamond film 63.

The $p^+$ diamond layers 64 are formed at the edges of each semiconducting diamond film 63, and an electrode 65 is formed on each of said $p^+$ layers 64. Said electrodes 65 are coated with an electrically insulating film 66, while an undoped diamond layer 67 is formed between the electrodes 65. A bioidentifier 68 is fixed on the undoped diamond layer 67 of the thermistor portion for heat measurement, and said bioidentifier 68 is further coated with a biomembrane 69.

As the temperature is increased, the resistance of said p-type semiconducting diamond film 63 is decreased, and therefore, the environmental temperature can be determined from the resistance value. In FIG. 16, thermistors for reference and heat measurement are placed side-by-side, and from the difference of the temperatures between the two thermistors, the concentration of chemical and bio-related substances in the sample can be determined.

FIG. 17 illustrates a biosensor in which the thermistors for reference and heat measurement are unified. The production process can be simplified by choosing the structure.

If the substrate 61 is not diamond, it is desirable that the thickness of said undoped diamond base layer 62 is between 1 and 20 μm, the thickness of said $p^+$ layer 64 is between 100 μm and 1 mm, and the thickness of said semiconducting diamond layer 63 is between 0.5 and 10 μm. There is no restriction in the distance between the electrodes, but it can be between about 1 μm and several mm. If said semiconducting diamond film 63 is of p-type and doped with boron, the desirable doping concentration is between $10^{15}$ and $10^{20}$ atom/cm$^3$.

When the transducer is of Hall effect-type or magnetic resistance-type, the concentration of chemical and bio-related substances in the sample can be determined by detecting magnetic changes caused by the reaction between the bioidentifier and the chemical and bio-related substances in the sample.

Figure 18:
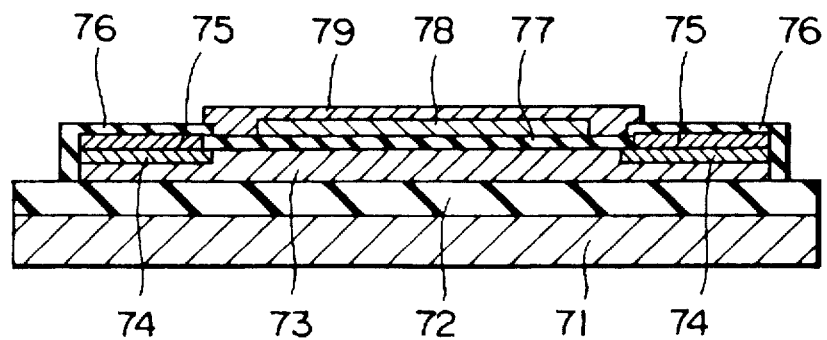
FIG. 18 is a cross-sectional view of a Hall effect-type diamond sensor provided in the embodiment of the present invention.
Figure 19:
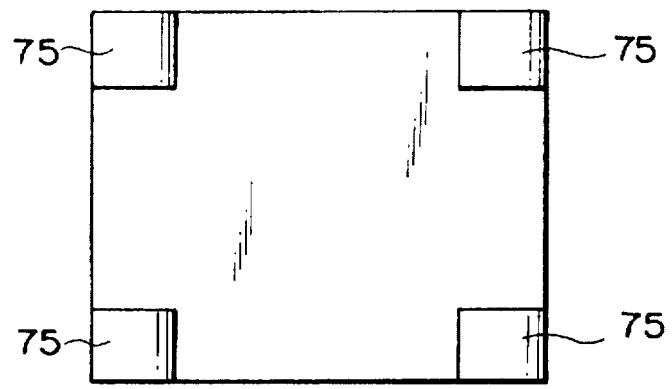
FIG. 19 is a top view showing a layout of the electrodes.
Figure 20:
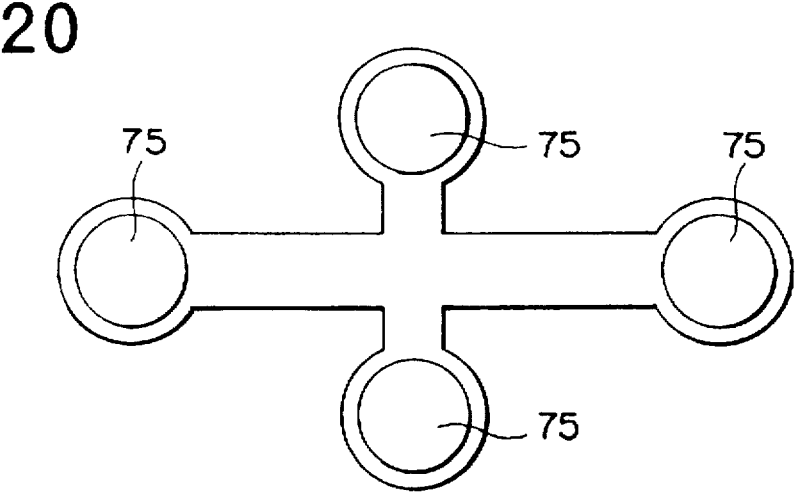
FIG. 20 is a top view showing another layout of the electrodes.

FIG. 18 is a cross-sectional view of a Hall effect-type sensor. FIGS. 19 and 20 show examples of electrode layout, where details are omitted except for the position of the electrode. Here, said undoped diamond layer 72 is formed on a substrate 71, and said semiconducting diamond layer 73 is formed on said undoped diamond layer 72. A $p^+$ diamond layer 74 is formed on the edge of the surface of said semiconducting diamond layer 73, and an electrode 75 is formed on the $p^+$ diamond layer 74. Each of said electrodes 75 is coated with an electrically insulating film 76, and an undoped diamond film 77 is formed between said electrodes 75 on which a bioidentifier 78 is fixed. Said bioidentifier 78 is further coated with a biomembrane 79.

If the substrate 71 is not diamond, it is desirable that the thickness of said undoped diamond base layer 72 is between 1 and 20 μm, the thickness of said $p^+$ layer 74 is between 100 μm and 1 mm, and the thickness of said semiconducting diamond layer 73 is between 0.5 and 50 μm. Most preferably, the distance between the electrodes is between 1 and 500 m. If said semiconducting diamond film 73 is p type and doped with boron, the preferable doping concentration is preferably between $10^{14}$ and $10^{18}$ atom/cm$^3$.

It is known that injection of carriers (electron and hole) into diamond film can generate a light with a short wavelength. Also, a photodetector can be made using diamond film. Therefore, a transducer for a biosensor can be made by using diamond film as the photoemission and/or photodetector device elements.

For example, if the photoemission phenomenon occurs due to the reaction between the bioidentifier and the chemical and bio-related substances in the sample, the light can be detected by the diamond photodetector.

Figure 21:
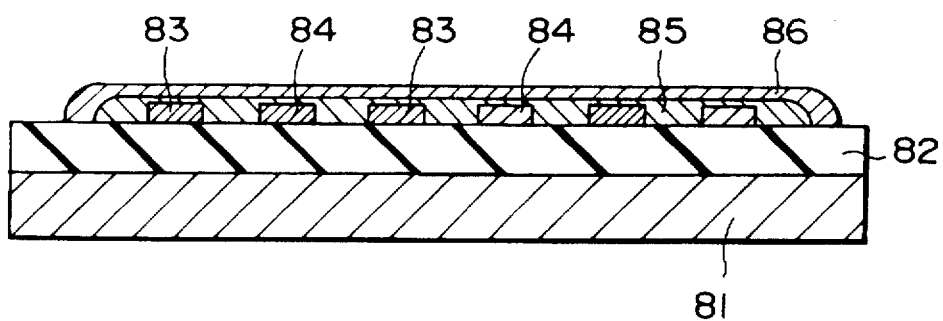
FIG. 21 is a cross-sectional view of a photosensor-type diamond sensor provided in the embodiment of the present invention.
Figure 22:
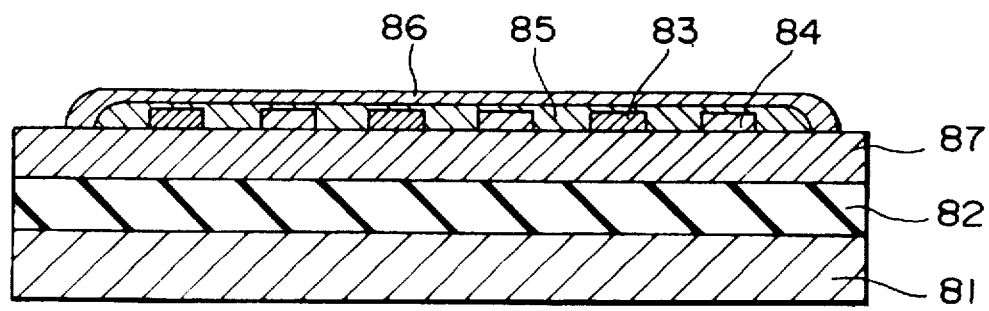
FIG. 22 is a cross-sectional view of another photosensor-type diamond sensor provided in the embodiment of the present invention.

Alternatively, the chemical and bio-related substances in the sample can be detected by the diamond photodetector by illuminating a light with a certain wavelength that is most sensitive to the substances from outside. Furthermore, a biosensor including the diamond emission portion on the substrate can be fabricated in a monolithic manner. FIGS. 21 and 22 are examples of such biosensors of photosensor type.

In the sensor illustrated in FIG. 21, an undoped diamond base layer 82 is deposited on a substrate 81, and plural first electrodes 83 and second electrodes 84 are laid out at an appropriate interval on said base layer 82. The interval area between the electrodes is filled with a bioidentifier 85 coated with a biomembrane 86.

In FIG. 22, a semiconducting diamond layer 87 is deposited on the undoped diamond layer 82.

As illustrated in FIGS. 21 and 22, a photoemission produced by the reactions between said bioidentifier 85 and the chemical or bio-related substances is detected by said diamond film 82 or said semiconducting diamond film 87, and the concentration of chemical or bio-related substances is determined by measuring the carriers (electron and hole) generated in the diamond films between said electrodes 83 and 84.

If the substrate 81 is not diamond, it is desirable that the thickness of said undoped diamond base layer 82 is between 1 and 50 μm, the thickness of said semiconducting diamond layer 87 is between 0.5 and 50 μm, and the distance between electrodes is between 1 and 50 μm. If said semiconducting diamond film 87 is of p type and doped with boron, the preferable doping concentration is between $10^{14}$ and $10^{19}$ atom/cm$^3$.

In any of the biosensors shown in the above embodiments, the sensitivity of the sensor can be increased by an illumination of light on the transducer. This is because the carrier concentration in diamond is increased by the illumination, and hence the signal intensity is increased.

In the above examples, a free-standing undoped diamond film can be used as a substrate for the sensor. In this case, the quality of the semiconducting diamond film grown on undoped diamond film is expected to be better than that grown on non-diamond substrate. If the substrate consists only of diamond film, it is desirable that the thickness is between 20 and 500 μm.

As has been described previously, bioidentifiers can be easily fixed on diamond. To this end, a direct application of the bioidentifier to diamond film surface is possible. However, it is recommended to fix the bioidentifier after the diamond film surface is chemically modified. It is also possible to chemically modify the diamond film surface to bond long-chain molecules or mediators (hereafter, referred to as the functional molecules), and then fix the bioidentifier.

For chemical modification of diamond surface, the following methods are possible: hydrogenation (—H), oxidation (=O, —O=O—, —OH—OH—, etc.), halogenation (—Cl), etc. The termination by hydroxyl (—OH), cyano (—CN), amino (—NH$_2$), carboxyl (—COOH), sulfuric add (SO$_3$), or nitro (NO$_2$) groups, and the termination using more than two kinds of substituents selected from these groups are also possible.

In order to fix a giant bioidentifier such as glucose oxidase on diamond, it is recommended to use a diamond surface that have been chemically modified using the above method and further modified by bonding such long chain molecules as hexamethyene diamine, rather than to use a chemically modified surface of diamond. In this way, a steric hindrance between the diamond surface and the giant bioidentifier can be avoided, and a stronger fixation of the giant bioidentifier is possible because of the chemical bonds between the long-chain molecules and the giant bioidentifier.

In order to chemically bind long chain molecules with the bioidentifier, it is desirable that at least one of hydroxyl, cyano, amino, carboxyl, sulfuric-acid, and nitro groups is contained in the long chain molecule. Hexamethylenediamine or its derivatives is such an example.

If a mediator (chemical substances and molecules to facilitate electron transport) layer is placed between the bioidentifier and the transducer, electrons produced by the reaction between the chemical and bio-related substances and the bioidentifier can move easily to the transducer via the mediator. Thus, the sensitivity of the sensor is increased, and the signal is not disturbed by the dissolved oxygen. As for mediators, ferrocen, quinone and their derivatives are available.

However, it should be noted that for the case of semiconducting diamond electrodes with a proper surface modification, electrons can be easily transported to the transducer even without such mediators, unlike ordinary metal electrodes.

Since diamond is quite inactive with chemical agents, even though the sensor is deteriorated, it can be revived by chemically removing the bioidentifier or both the bioidentifier and the functional molecules, and then fixing the bioidentifier or both the functional molecules and the bioidentifier on the diamond electrode. This prevents environmental pollution due to harmful waste, and reduce production cost Sometimes, toxic substances are contained in the sample to deactivate the bioidentifier. In the present invention, such a disturbance can be avoided by coating the surface of the bioidentifier with a biomembrane of more than a monolayer.

Figure 23:
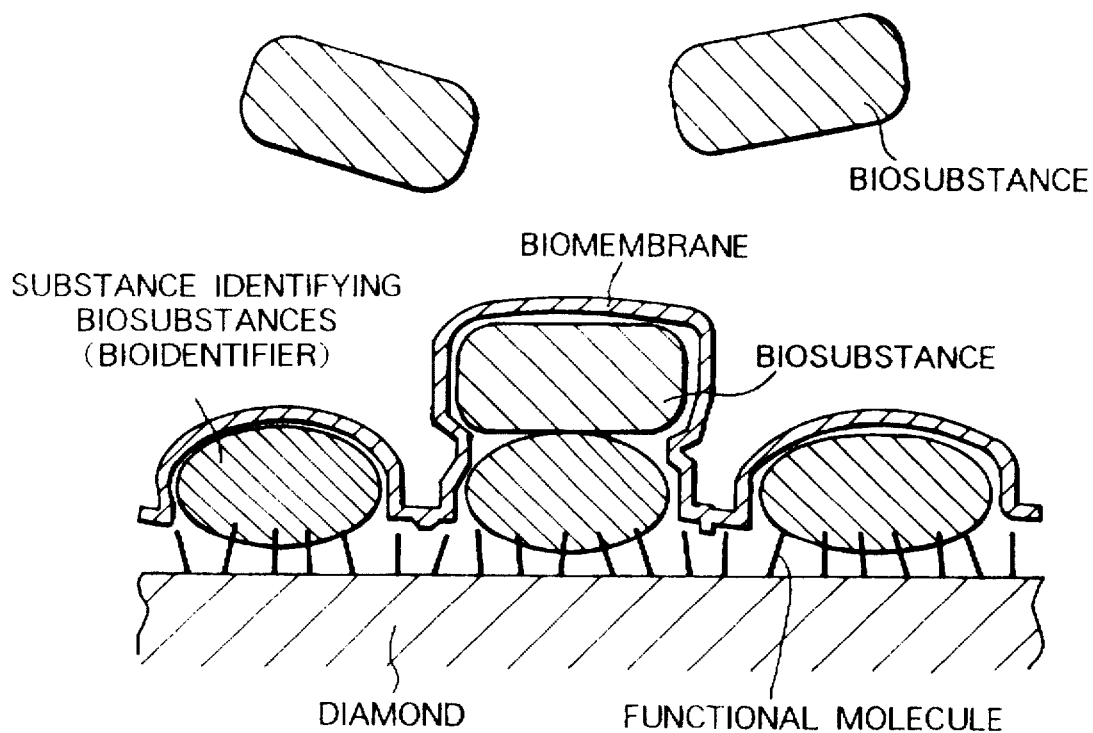
FIG. 23 illustrates the functions of the biomembrane.

FIG. 23 illustrates the function of the biomembrane. Initially, the biomembrane protects the sensor surface from the intrusion of the toxic substances. When the bio-related substance to be detected is adsorbed at the biosensor surface, the biomembrane covers the substance to prevent the direct contact to the biosensor. Phosphatidylcholine, phosphatidylserine and the like are typical of such biomembranes.

The following Tables 1–3 show bioidentifiers and chemical substances and biosubstances that the bioidentifiers can detect. Table 1 shows the sensors for bio-substances and chemical substances, Table 2 shows the sensors for lipids, and Table 3 shows the sensors using microorganisms.

TABLE 1

Bio-substance, Sensor for detection of chemical substances

| Substance to be detected | Identifying substance | Fixing method | Electrode | Stability (day) | Reaction time (minute) | Measurement range (mg/l) |
|---|---|---|---|---|---|---|
| Glucose | Glucose oxidase | Covalent bonding method | Oxygen electrode | 100 (Measurement of more than 1000 times possible) | 1/6 | $1-5 \times 10^2$ |
| Maltose | Glucoamylase | Covalent bonding method | Platinum electrode | — | 6–7 | $10^{-2}-10^2$ |
| Galactose | Galactose oxidase | Adsorption method | Platinum electrode | 20–40 | | $10-10^3$ |
| Ethanol | Alcoholoxidase | Bridged method | Oxygen electrode | 120 | 1/2 | $5-10^3$ |
| Phenol | Tyrosinase | Comprehensive method | Platinum electrode | — | 5–10 | $5-2 \times 10^2$ |
| Catechol | Catechol 1,2-oxygenase | Bridged method | Oxygen electrode | 30 | 1/2 | $5-2 \times 10^2-10$ |
| Pyruvic acid | Pyruvic acid oxidase | Adsorption method | Oxygen electrode | 10 | 2 | $10-10^3$ |
| Uric acid | Uricase | Bridged method | Oxidized electrode, ammonia gas electrode | 120 | 1/2 | $10-10^3$ |
| L-amino acid | L-amino acid oxidase | Covalent binding method | Ammonia gas electrode, Ammonium ion electrode | 70 | — | $5-10^2$ |
| D-amino acid | D-amino acid oxidase | Comprehensive method | Ammonium ion electrode | 30 | 1 | $5-10^3$ |
| L-glutamine | Glutaminase | Adsorption method | Ammonium ion electrode | 2 | 1 | $10-10^4$ |

TABLE 1-continued

Bio-substance, Sensor for detection of chemical substances

| Substance to be detected | Identifying substance | Fixing method | Electrode | Stability (day) | Reaction time (minute) | Measurement range (mg/l) |
|---|---|---|---|---|---|---|
| L-Glutamine | Glutamate dehydrogenase | Adsorption method | Ammonium ion electrode | 2 | 1 | $10-10^4$ |
| L-asparagine | Asparaginase | Comprehensive method | Ammonium ion electrode | 30 | 1 | $5-10^3$ |
| L-tyrosine | L-tyrosine decarboxylase | Adsorption method | Carbonic acid gas electrode | 20 | 1–2 | $10-10^4$ |
| ATP | Antibacterial ATPase | Polyvinyl butyral, Glutaric anhydride | — | — | — | 0.2–1.0 (mM) |
| Acetylcholine | Acetylcholine receptor | Polyvinyl butyral | — | — | — | 0.1–10 ($\mu M$) |
| HSA | Anti-HSA antibody | Polyvinyl butyrase, Glutaric aldehyde | — | — | — | 1.4–14 ($\mu M$) |

TABLE 2

Sensor for detection of lipid

| Substance to be detected | Identifying substance | Fixing method | Electrode | Stability (day) | Reaction time (minute) | Measurement range (mg/l) |
|---|---|---|---|---|---|---|
| Cholesterol | Cholesterol esterase | Covalent binding method | Platinum electrode | 30 | 3 | 10–500 |
| Neutral lipid | Lipase | Covalent binding method | pH electrode | 14 | 4 | 5–50 |
| Phospholipid | Phospholipase | Covalent binding method | Platinum electrode | 30 | 2 | — |
| Monoamine | Monoamine oxidase | Comprehensive method | Oxygen electrode | <7 | 4 | 10–100 |
| Penicillin | Penicillinase | Comprehensive method | pH electrode | 7–14 | 0.5–2 | $10 \times 10^3$ |

TABLE 3

Biosensor using microorganism

| Substance to be detected | Identifying substance | Fixing method | Electrode | Stability (day) | Reaction time (minute) | Measurement range (mg/l) |
|---|---|---|---|---|---|---|
| Glucose | Pseudomonas Fluorescence | — | Oxygen electrode | 14 | 10 | 3–20 |
| Catabolic sugar | Brevibacterium lactofermentum | — | Oxygen electrode | 20 | 10 | 20–200 |
| Acetic acid | Trichosporon brassicae | — | Oxygen electrode | 30 | 15 | 10–200 |
| Ammonia | Nitrifying bacteria | — | Oxygen electrode | 20 | 5 | 3–45 |
| Methanol | Unidentified bacteria | — | Oxygen electrode | 30 | 15 | 3–22 |
| Ethanol | Trichosporon brassicae | — | Oxygen electrode | 30 | 15 | 3–30 |
| Nystatin | Saccharomyces | — | Oxidized | — | 60 | 1.2–800 |

TABLE 3-continued

Biosensor using microorganism

| Substance to be detected | Identifying substance | Fixing method | Electrode | Stability (day) | Reaction time (minute) | Measurement range (mg/l) |
|---|---|---|---|---|---|---|
| | cerevisiae | | electrode | | | |
| Mutagen | Bacillus subtilis | — | Oxidized electrode | — | 60 | 1–10 |
| Nitrite | Nitrobactersp | — | Oxygen electrode | 24 | 4 | 51–250 |
| Vitamin B12 | Escherichia coli | — | Oxygen electrode | 25 | 2 | $5 \times 10^{-3}$–$2.5 \times 10^{-2}$ |
| Methane | Methyromonas flagellata | — | Oxygen electrode | 30 | 0.5 | 0.2–100 |
| BOD | Trichosporon cutaneum | — | Oxygen electrode | 30 | 10 | 3–30 |
| Vitamin B1 | Lactobacillus fermenti | — | Fuel cell | 60 | 360 | $10^{-3}$–$10^{-2}$ |
| Formic acid | Clostridium botyricum | — | Fuel cell | 30 | 10 | 1–1000 |
| Cephalosporin | Citrobacter freundii | — | pH cell | 7 | 10 | 60–500 |
| Nicotinic acid | Lactobacillus arabinosus | — | pH cell | 30 | 60 | $10^{-2}$–5 |
| Glutamic acid | Escherichia coli | — | $CO_2$ cell | 20 | 5 | 8–800 |
| Lysine | Escherichia coli | — | $CO_2$ cell | 20 | 5 | 10–100 |

Usually, the voltage between the electrodes of diode-type biosensors is set to within 75 V, and in many cases, it is within 71 V. If the voltage of more than 75 V is applied to an ISFET made of silicon semiconductor, the FET is broken down. However, since diamond has a high breakdown voltage, it is fully resistant to a voltage of more than 75 V in diode- and transistor-type sensors. This feature of diamond biosensors is especially important for a high sensitivity measurement, because the voltage must be maximized. Diamond biosensors in the present invention can be operated even at a voltage of more than 710 V. According to the study by the present inventors, the maximum voltage to diamond biosensors is 750 V, and preferably 75 to 720 V.

So far, diamond transducers with a single function have been described. However, in the present invention, sensors with the same or different functions can be fabricated on the same substrate. For example, a biosensor with plural diode-type sensors with the bioidentifier of the same kind on the same substrate is more reliable than a single diode-type sensor.

Furthermore, by using different bioidentifiers on the same substrate, more than two chemical substances and biosubstances can be detected with one biosensor. Such a biosensor is very useful for the measurement of two or more substances in the sample at a time. Odor, taste, and freshness sensors are such examples. If a diode-type sensor is combined with a temperature or pH sensor, real time corrections due to temperature or pH are possible.

Diamond films described above can be those deposited by vapor-phase synthesis on the surface of natural or man-made bulk diamond crystal substrate. They can also be ordinary polycrystalline diamond films, highly oriented diamond films, and heteroepitaxial diamond films deposited on non-diamond substrates, such as silicon, silicon nitride, silicon carbide, refractory metals, and the like.

Since the chemical reactivity and the surface structure of diamond are different for different crystal planes, the diamond surface for the biosensor must be carefully selected for chemical modification and binding of functional molecules, and hence for the best sensor performance. In the present invention, it was found that biosensors with a good linearity in the current-voltage characteristic and a good signal-to-noise ratio are achieved, if the diamond film surface consists of either (111) or (100) crystal faces.

The biosensors shown in the embodiments of the present invention were actually fabricated to investigate its characteristics. The following are descriptions of the results:

EXAMPLE 1

Diode-type sensor
(1A) Fabrication of diamond device

An undoped diamond film of 10 μm thickness was deposited by microwave plasma CVD for 20 hours using 1–5% methane and 0.1–2% oxygen diluted with hydrogen (total flow rate, 100 sccm) as the source gas on a silicon nitride substrate of 1 cm square, which had been subject to a buff-polishing with diamond powder. In the CVD, the substrate temperature was maintained at 800° to 850° C., and the gas pressure at 30 to 60 Torr.

As a working electrode, a B-doped p-type semiconducting diamond film with a width of 10 μm, a length of 2 mm, and a thickness of 2 μm was deposited on the substrate at a pitch of 20 μm using the selective deposition technology. The diamond CVD was similarly done using 1–5% methane, 0–2% oxygen and 0.1–20 ppm of diborane ($B_2H_6$) diluted with hydrogen as the source gas using microwave plasma CVD. The synthesis time was 10 hours.

Then, a platinum film of 20 μm width, 2 mm length and 1000 Å thickness was formed by photolithography.
(1B) Fixation of bioidentifier The specimen was put in a radio-frequency plasma apparatus, and the diamond surface was oxidized by oxygen gas at a pressure of 0.1 Torr for 10 minutes. Then, the specimen was soaked in a hexamethylenediamine solution, and left at a temperature between 50° C. and 90° C. for 10 hours for chemical binding. The specimen was then soaked in a 10% glutaraldehyde, 0.1M phosphoric add buffer solution of pH 7 for 2 hours, and rinsed in the buffer solution.

In order to fix glucoseoxidase, the electrodes, except for the working electrode, were masked with photoresist films, and the specimen was soaked overnight in a phosphoric add buffer solution suspended with 1% glucoseoxidase. The specimen was then rinsed in the buffer solution, and the photoresist film was removed using organic solvents.

(1C) Protection of bioidentifier

A 0.1M phosphoric add buffer solution of pH 7 and phosphatidylcholine, which is a biomembrane substance, were mixed and suspended by an ultrasonic treatment. The specimen with said glucoseoxidase fixed was soaked overnight in this solution.

(1D) Evaluation of sensor characteristics

The diode-type sensor fabricated above was soaked in a 0.1M sodium chloride solution containing glucose, and 1 V voltage was applied between the working and the counter electrodes, and between the reference and counter electrodes. The current was measured by changing the glucose concentration. The obtained data was shown by curve A in FIG. 24.

Figure 24:
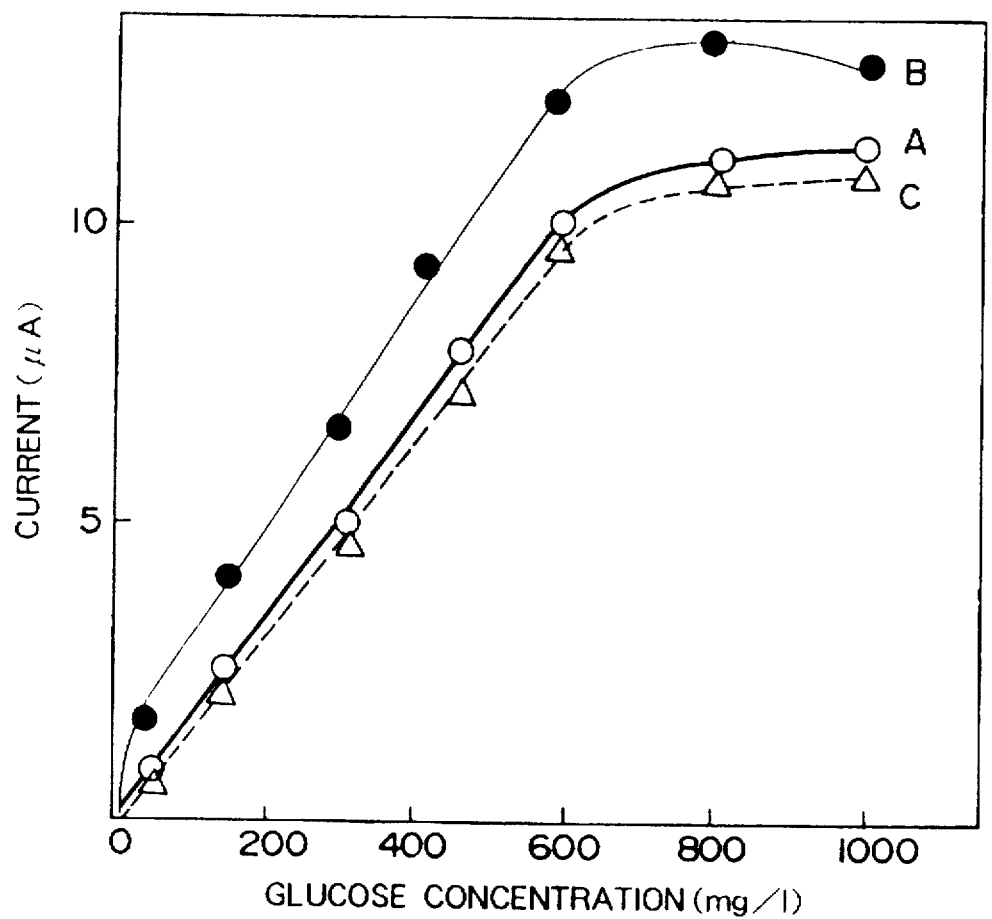
FIG. 24 is a graph showing characteristics of a diode-type sensor.

In FIG. 24, the value of the current means the difference in currents between the working and the counter electrodes and between the reference and the counter electrodes. The current values were linearly plotted for the glucose concentration between 50 mg/liter and 600 mg/liter.

(1E) Effects of light illumination

The same measurement as in (1D) was done by illuminating the specimen with a light from a mercury lamp. The result is shown by curve B in FIG. 24. The current increased by 2 to 3 μA for the glucose concentration between 50 mg/liter and 600 mg/liter.

(1F) Characteristics of revived sensor

The glucose oxidase of the biosensor was removed by ultrasonic treatment in a buffer solution, and the sensor was revived by the processes described in (1B), except for the oxygen plasma treatment. Then, the characteristics of the sensor were evaluated. The result is shown by curve C in FIG. 24. It is seen that the current was the same as those measured before.

(1G) Effects of biomembrane

Figure 25:
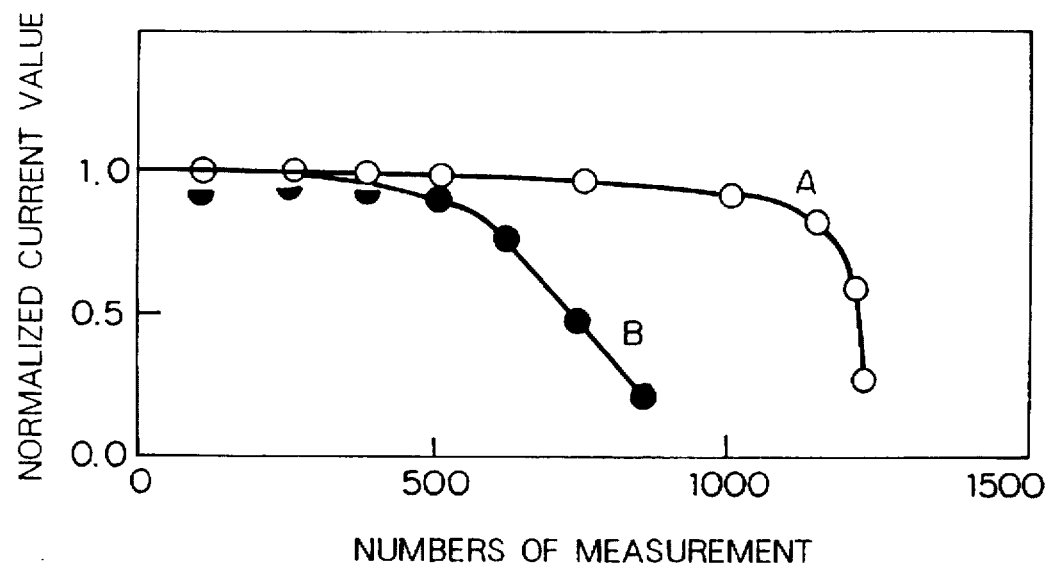
FIG. 25 is a graph showing the effects of the biomembrane.

In FIG. 25, curve A shows the result in which the sensor was coated with a biomembrane, and curve B shows the result without the coating. For the case of coating with the biomembrane (curve A), the value of current was reduced by about 10% after a repeated use of 1000 times. For the case without coating (curve B), the value of current was reduced by about 10% after a repeated use of about 500 times. As a result, it was concluded that the lifetime of the sensor was doubled by coating the sensor surface with the biomembrane.

EXAMPLE 2

Microarray sensor

A microarray sensor was fabricated by the same processes as in Example 1. The width and the length of the active area of the semiconducting diamond film of the working electrode were 10 μm and 300 μm, respectively, and the width of the undoped diamond film between the electrodes was 10 μm. Fifty pieces of this unit were formed on the same substrate. By using a known method, glucose oxidase was fixed on the surface of the undoped diamond film, and then the biomembrane was coated.

An evaluation of the sensor characteristics showed that the current was proportional to the area of the electrode as in the process 1D in Example 1.

EXAMPLE 3

Transistor-type sensor

As shown in Nishimura et al., Advances in New Diamond Science and Technology, edited by S. Sato et al. (MYU, Tokyo, 1994) p. 725, two MiS-type FETs, where the distance between the source and drain electrodes was 10 μm and the gate width was 500 μm, were fabricated on a single crystal diamond substrate.

Figure 26:
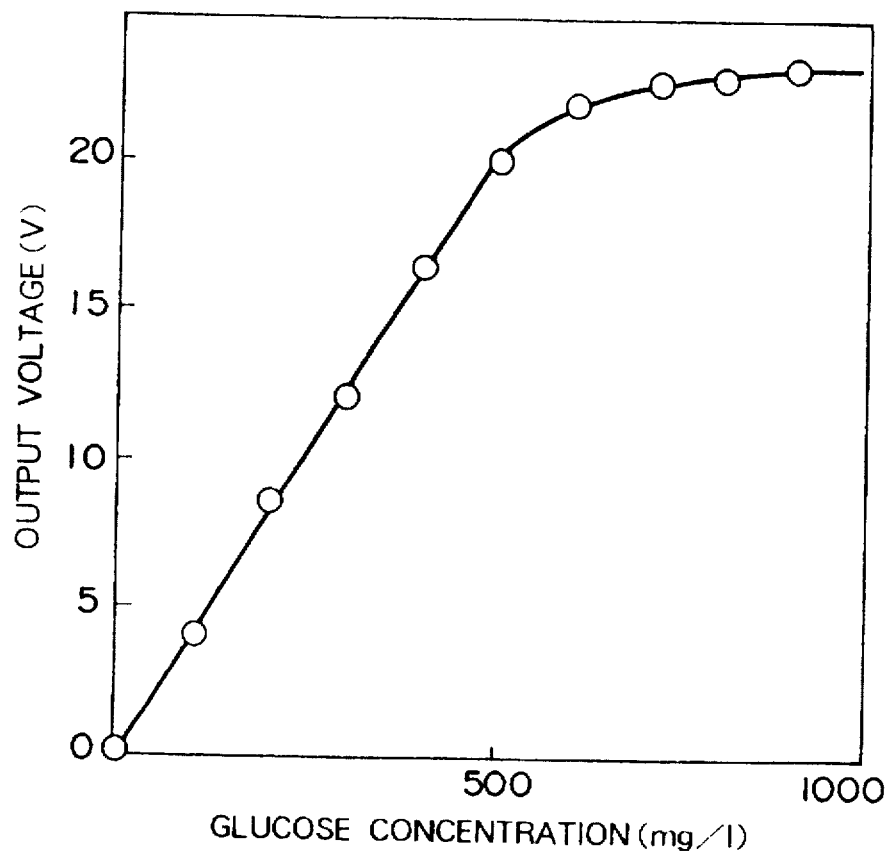
FIG. 26 is a graph showing the output voltage of a transistor-type sensor.
Figure 27:
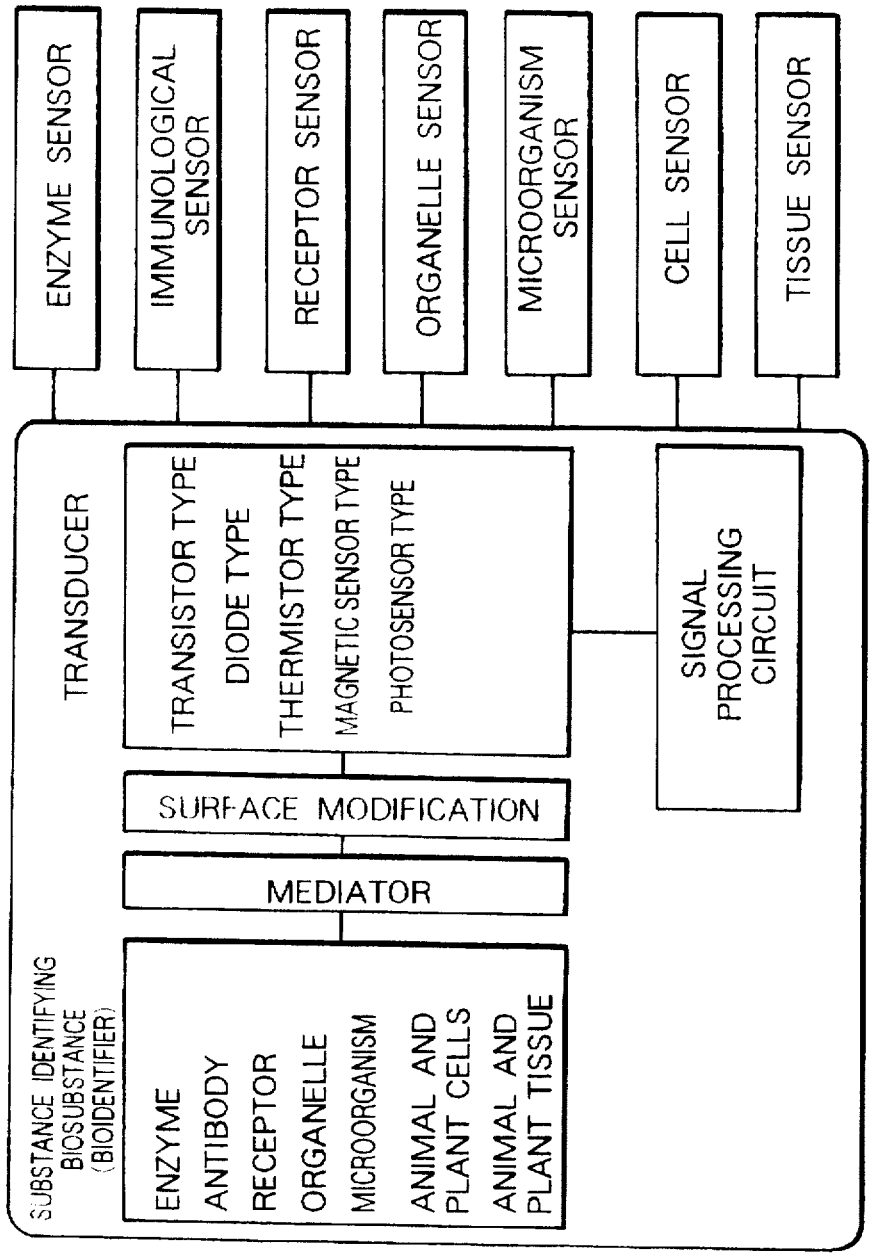
FIG. 27 illustrates a concept of biosensors in relation to the bioidentifiers.

Glucose oxidase was fixed only on one of the FETs in the same manner as the processes 1B and 1C in Example 1. The other FET was used as a reference. When the current between the source and drain electrodes on FETs for measurement and reference was 10 μA, the voltage difference between the source and drain electrodes of the two FETs was measured by changing the glucose concentration. The result is shown in FIG. 26.

In the present invention, since the bioidentifier was fixed on diamond film, the biosensor has high sensitivity and fast response to a variety of chemical substances and biosubstances. Furthermore, by fabricating both the transducer and peripheral circuits using semiconducting diamond film, practical chemical sensors and biosensors have been achieved.

The sensors provided by the present invention can be utilized as chemical, odor, taste, and freshness sensors, as well as biosensors, which can contribute in such technological fields as medical industries, food processing and control, industrial processes, environmental monitoring, and the like.

What is claimed is:

1. A diamond film biosensor comprising:
   a transducer having a semiconducting diamond film and/or undoped diamond film; and
   a bioidentifier fixed to and covering at least a portion of a surface of said semiconducting diamond film and/or undoped diamond film.

2. The diamond film biosensor according to claim 1, wherein peripheral circuits of said transducer also include said semiconducting diamond film and/or undoped diamond film.

3. The diamond film biosensor according to claim 1, wherein said transducer includes a working electrode, a counter electrode, and a reference electrode, wherein said working electrode comprises said semiconducting diamond film to which said bioidentifier is fixed.

4. The diamond film biosensor according to claim 1, wherein said transducer includes a working electrode, a counter electrode, and said undoped diamond film to which said bioidentifier is fixed, said undoped diamond film being positioned between the working electrode and the counter electrode.

5. The diamond film biosensor according to claim 1, wherein said transducer comprises a transistor including said semiconducting diamond film to which said bioidentifier is fixed.

6. The diamond film biosensor according to claim 1, wherein said transducer has a temperature-sensitive portion including said semiconducting diamond film to which said bioidentifier is fixed.

7. The diamond film biosensor according to claim 1, wherein said transducer has a magnetically sensitive portion including said semiconducting diamond film to which said bioidentifier is fixed.

8. The diamond film biosensor according to claim 1, wherein said transducer has a light emitting portion and/or light sensing portion including said semiconducting diamond film to which said bioidentifier is fixed.

9. The diamond film biosensor according to claim 1, wherein the transducer is on a substrate comprising an undoped diamond film or a semiconducting diamond film.

10. The diamond film biosensor according to any one of claims 1 to 9, wherein the surface of said semiconducting diamond film and/or undoped diamond film to which the bioidentifier is fixed is hydrogenated, oxidized, or halogenated, or is chemically modified with two or more of substituents selected from groups consisting of hydroxyl, cyano, amino, carboxyl, sulfuric-acid, and nitro groups, prior to fixing said bioidentifier.

11. The diamond film biosensor according to claim 10, wherein functional molecules are chemically bound to said semiconducting diamond film and/or undoped diamond film at said surface to which said bioidentifier is fixed.

12. The diamond film biosensor according to claim 11, wherein said functional molecules contain two or more substituents selected from groups consisting of hydroxyl, cyano, amino, carboxyl, sulfuric-acid, and nitro groups.

13. The diamond film biosensor according to claim 11, wherein said functional molecule is hexamethylenediamine or its derivatives.

14. The diamond film biosensor according to claim 11, wherein said functional molecule is ferrocen, quinone, or their derivatives.

15. The diamond film biosensor according to any one of claims 1 to 9, wherein more than a monolayer of a biomembrane is coated on a surface of said bioidentifier.

16. The diamond film biosensor according to claim 1, wherein said semiconducting diamond film and/or undoped diamond film is deposited by vapor-phase synthesis using natural diamond or artificial synthetic diamond crystal as substrates.

17. The diamond film biosensor according to claim 1, wherein the semiconducting diamond film and/or undoped diamond film is formed as a single layer film or as a multilayer film.

18. The diamond film biosensor according to claim 1, wherein said semiconducting diamond film and/or undoped diamond film are polycrystalline highly oriented, or heteroepitaxial.

19. The diamond film biosensor according to any one of claims 1 to 9 and 16 to 18, wherein the surface of said semiconducting diamond film and/or undoped diamond film comprises (111) or (100) crystal surfaces.

* * * * *